United States Patent
Cho et al.

(10) Patent No.: US 6,967,213 B2
(45) Date of Patent: Nov. 22, 2005

(54) ISOTHIAZOLE DERIVATIVES, PROCESS FOR THE PREPARATION THEREOF, AND PHARMACEUTICAL COMPOSITION INCLUDING THE SAME

(75) Inventors: Il Hwan Cho, Seoul (KR); Dong Hyun Ko, Gyeonggi-do (KR); Myeong Yun Chae, Gyeonggi-do (KR); In Ki Min, Gyeonggi-do (KR); Young Hoon Kim, Seoul (KR); Young Mee Chung, Gyeonggi-do (KR); Hyun Jung Park, Jeollabuk-do (KR); Ji Young Noh, Busan (KR); Il Hwan Kim, Daejeon (KR); Hyung Chul Ryu, Gyeonggi-do (KR); Sang Wook Park, Gyeonggi-do (KR); Sung Hak Jung, Seoul (KR); Jong Hoon Kim, Gyeonggi-do (KR)

(73) Assignee: CJ Corp., Seoul (KR)

( * ) Notice: Subject to any disclaimer, the term of this patent is extended or adjusted under 35 U.S.C. 154(b) by 30 days.

(21) Appl. No.: 10/681,919

(22) Filed: Oct. 9, 2003

(65) Prior Publication Data

US 2004/0072884 A1 Apr. 15, 2004

(51) Int. Cl.⁷ ................. A61K 31/425; C07D 275/02
(52) U.S. Cl. ................... 514/372; 514/372; 548/214
(58) Field of Search ................ 548/214; 514/372

(56) References Cited

U.S. PATENT DOCUMENTS 5,466,823 A   11/1995 Talley et al.
5,633,272 A   5/1997 Talley et al.
5,840,746 A * 11/1998 Ducharme et al. .......... 514/438

OTHER PUBLICATIONS

In re Wood (CCPA) 199 USPQ 137 (1978).*

* cited by examiner

Primary Examiner—Joseph K. McKane
Assistant Examiner—Janet L. Coppins
(74) Attorney, Agent, or Firm—Swanson & Bratschun, L.L.C.

(57) ABSTRACT

The present invention relates to an isothiazole derivative of the following formula 1 or nontoxic salt thereof:

Formula 1

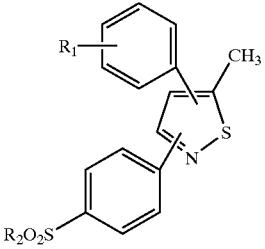

wherein, $R_1$ is hydrogen, alkoxy group or halogen group; $R_2$ is methyl or amino group.

According to the present invention, isothiazole derivative or nontoxic salt thereof having antipyretic, analgesic and antiphlogistic activity and an improved side effect; process for the preparation thereof; and pharmaceutical composition including the same can be provided.

3 Claims, No Drawings

ISOTHIAZOLE DERIVATIVES, PROCESS FOR THE PREPARATION THEREOF, AND PHARMACEUTICAL COMPOSITION INCLUDING THE SAME

RELATED APPLICATIONS

This application claims priority to Korean Application No. 2002-0062689, filed Oct. 15, 2002, entitled "Isothiazole Derivatives, Process for the Preparation thereof, and Pharmaceutical Composition Including the Same," which is incorporated herein by reference in its entirety.

BACKGROUND OF THE INVENTION

1. Field of the Invention

The present invention relates to isothiazole derivatives with antipyretic, analgesic and antiphlogistic effect, or non-toxic salts of the isothiazole derivatives, process for the preparation thereof, and pharmaceutical composition including the same as an effective component.

2. Background of the Related Art

Most of non-steroid anti-inflammatory drugs represent actions such as anti-inflammation, analgesic, and antipyretic activity by inhibiting the enzymatic activity of cyclooxygenase or prostaglandin G/H synthase. In addition, they can suppress the uterine contraction induced by hormones and the cell proliferation in several kinds of cancers. Firstly, only cyclooxygenase-1 (COX-1), found in cow as a constitutional enzyme, was known. But recently, cyclooxygenase-2 is identified to be discriminated clearly from cyclooxygenase-1 and can be provoked easily by mitogen, endotoxin, hormones, growth factors, cytokines and the like.

Prostaglandins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like, and thus plays an important role in pathological effects of prostaglandin. Therefore, selective inhibitors against cyclooxygenase-2 are expected to have no side effect on account of the functional mechanism compared with the anti-inflammatory drugs such as conventional non-steroid agents and to represent actions such as antiphlogistic, analgesic and antipyretic activity. Furthermore, it is estimated to suppress the uterine contraction induced by hormones and the cell proliferation in several kinds of cancers. Especially, it probably has a few side effects such as gastrointestinal toxicity, renal toxicity and the like. Also, it is assumed to prevent the synthesis of contractive prostanoids, and thus inhibit the contraction of smooth muscle induced by the prostanoid. Hence, it can be applied usefully to treat a premature birth, dysmenorrhea, asthma and several diseases associated with eosinophilic leukocytes. Besides, it can be widely exploited to cure osteoporosis, glaucoma, large intestine cancer, prostatic carcinoma and athymia, which has been disclosed in many references, especially the usefulness of selective inhibitors against cyclooxygenase-2 (References: John Vane, "Towards a better aspirin" in Nature, Vol.367, p215–216, 1994; Bruno Battistini, Regina Botting and Y. S. Bakhle, "COX-1 and COX-2: Toward the Development of More Selective NSAIDs" in Drug News and Perspectives, Vol.7, p501–512, 1994; Urology, Vol.58, p127, 2001; David B. Reitz and Karen Seibert, "Selective Cyclooxygenase Inhibitors" in Annual Reports in Medicinal Chemistry, James A. Bristol, Editor, Vol. 30, p179–188, 1995).

The selective inhibitors against cyclooxygenase-2 have been reported to have various structure forms. Among these, the diaryl heterocycle structure, namely a tricyclic system, has been studied most frequently and exploited to construct a lot of candidate substances. In this structure, it is essential that sulfonamide or methanesulfone group exist onto one phenyl group.

U.S. Pat. No. 5,466,823 disclosed celecoxib, the compound of the following formula 36. The celecoxib is a substituted pyrazolyl benzonesulfonamide derivative.

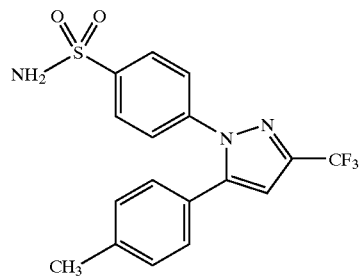

Formula 36

WO Pub. No. 95/00501 disclosed rofecoxib, the compound of the following formula 37. The rofecoxib has the same diaryl heterocycle structure as celecoxib of the formula 36, but the heterocycle structure is furanone structure.

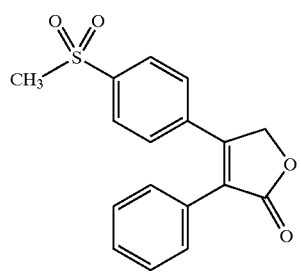

Formula 37

U.S. Pat. No. 5,633,272 disclosed valdecoxib, the compound of the following formula 38. The valdecoxib has the same phenyl sulfonamide structure as celecoxb of the formula 37, but the heterocycle structure is isoxazole structure.

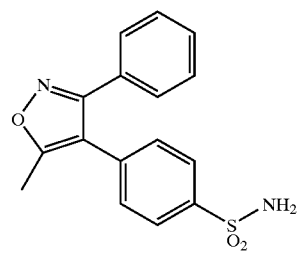

Formula 38

The forgoing compounds of the formula 36, 37 and 38 have antiphlogistic and analgesic effect without side effects comparing with the conventional non-steroid anti-inflammatory drugs as a selective cyclooxygenase-2 inhibitor.

SUMMARY OF THE INVENTION

Based upon the above technical backgrounds, the inventors of the present invention have tried in order to develop novel compounds as a highly selective cyclooxygenase-2 inhibitor. As a result, it is found that isothiazole derivatives satisfy such a purpose.

Therefore, an object of the present invention is to provide isothiazole derivatives or nontoxic salts of isothiazole derivatives.

Another object of the present invention is to provide a method for preparing isothiazole derivatives or nontoxic salts of isothiazole derivatives.

And a further object of the present invention is to provide pharmaceutical compositions with antipyretic, analgesic and antiphlogistic activity containing isothiazole derivatives or nontoxic salts of isothiazole derivatives as an effective component.

Hereinafter, the present invention will be described more clearly.

The present invention relates to an isothiazole derivative of the following formula 1 or its nontoxic salt.

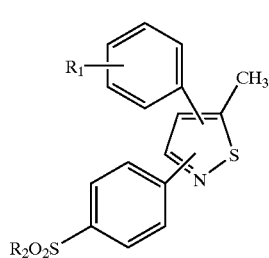

Formula 1 wherein, $R_1$ is hydrogen, alkoxy or halogen; and $R_2$ is methyl or amino group.

The compound of the present invention can be existed as a nontoxic salt form, wherein the nontoxic salt means a pharmaceutically acceptable nonpoisonous salt including an organic salt and inorganic salt.

Also, the compound of the present invention can be existed as a pharmaceutically acceptable salt form of an organic acid or inorganic acid. The organic acid or inorganic acid includes, but is not limited to, acetic acid, adipic acid, aspartic acid, 1,5-naphthalenedisulfonic acid, benzenesulfonic acid, benzoic acid, camposulfonic acid, citric acid, 1,2-ethanedisulfonic acid, ethanesulfonic acid, ethylenediaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalenedisulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid and 10-undecenoic acid. And preferable acids are succinic acid, hydrobromic acid, hydrochloric acid, maleic acid, methanesulfonic acid, phosphoric acid, sulfuric acid or tartaric acid.

More preferably, the isothiazole derivative or nontoxic salt thereof according to the present invention can be a compound selected from a group consisting of
4-(4-fluorophenyl)-3-(4-methanesulfonylphenyl)-5-methyl-isothiazol,
4-(5-methyl-3-phenyl-isothiazole-4-yl)-benzonesulfonamide,
4-[3-(4-bromophenyl)-5-methyl-isothiazlole-4-yl]-benzenesulfonamide,
4-[3-(4-methoxyphenyl)-5-methyl-isothiazole-4-yl]-benzenesulfonamide,
4-[3-(4-fluorophenyl)-5-methyl-isothiazole-4-yl]-benzenesulfonamide,
4-(4-methanesulfonylphenyl)-5-methyl-3-phenyl-isothiazole,
3-(4-bromophenyl)-4-(4-methanesulfonylphenyl)-5-methyl-isothiazole,
3-(4-methoxyphenyl)-4-(4-methanesulfonylphenyl)-5-methyl-isothiazole, and
3-(4-fluorophenyl)-4-(4-methanesulfonylphenyl)-5-methyl-isothiazole; or nontoxic salt thereof.

The present invention includes a method for preparing the compound of the following formula 1a including the reaction step for adding ammonia water to the compound of the following formula 7.

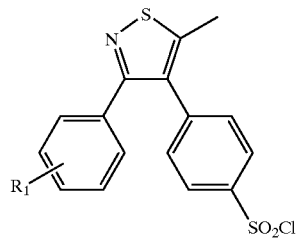

Formula 7

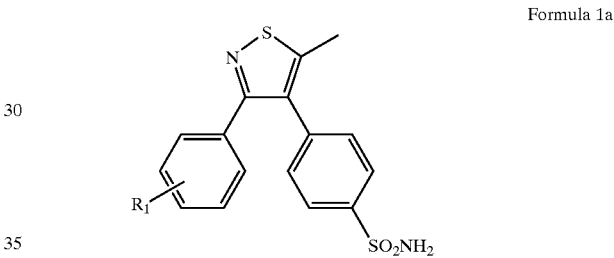

Formula 1a wherein $R_1$ is hydrogen, alkoxy or halogen.

The solvent used in the reaction includes, but is not limited to, dichloromethane, tetrahydrofuran (THF), benzene, toluene and the like.

The reaction can be accomplished by reacting at room temperature or by refluxing at boiling point depending upon compounds.

Also, the present invention includes a method for preparing the compound of the following formula 1b including the step for reacting the compound of the formula 7 with hydrazine and methyl iodide.

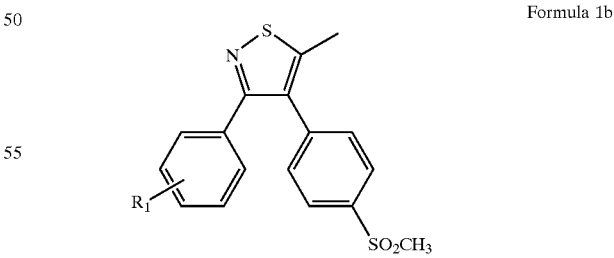

Formula 1b

The solvent used in the reaction includes, but is not limited to, dichloromethane, THF, benzene and the like.

The reaction can be accomplished by reacting at room temperature or by refluxing at boiling point depending upon compounds.

The compound of the formula 7 can be prepared as illustrated schematically in the following reaction formula 1.

Reaction Formula 1

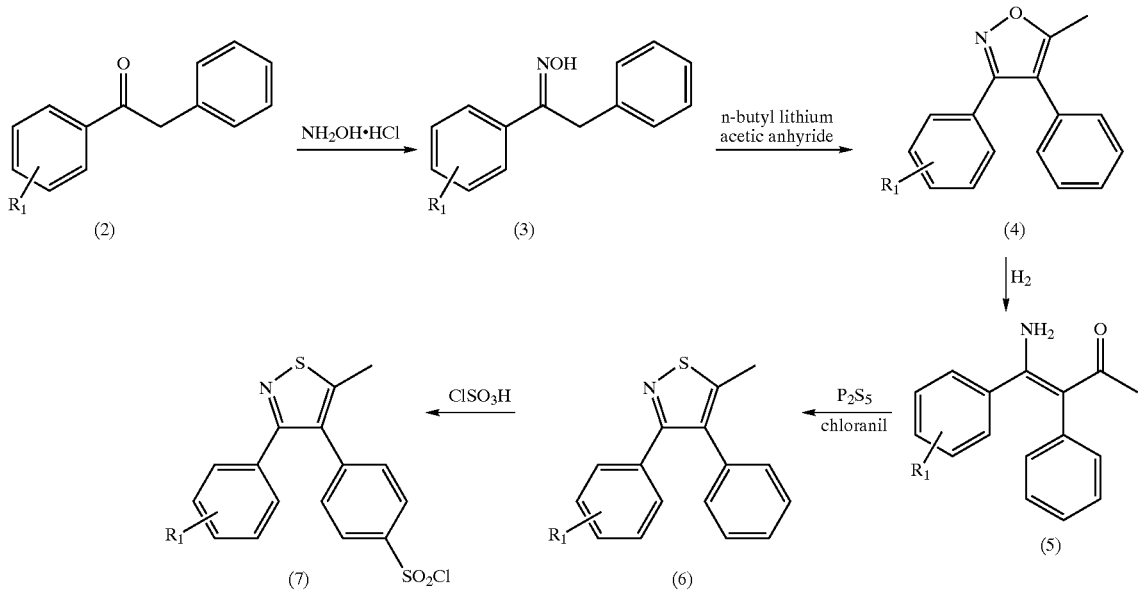

As demonstrated in the above reaction formula 1, the compound of the formula 7 can be prepared through five steps.

In the first step, dioxybenzoine (2) as initial material is reacted with hydroxylamine hydrochloride to prepare oxime compound (3). A base used in the above reaction can be selected from, but not limited to, sodium acetate, potassium hydroxide, sodium hydroxide, potassium carbonate and the like. Among these, potassium hydroxide can be used more preferably. The solvent used in this step procedure can be a conventional solvent used in an organic synthesis. Representative examples of such solvents are, but not limited to, toluene, ethanol, methanol, dimethylformamide, n-methylpyrrolidione and the like. Among these, ethanol is more preferable.

In the second step, oxime compound (3) from the first step is reacted with n-butyl lithium and acetic anhydride to prepare isoxazole compound. A solvent used in the present reaction can be a conventional non-reactive organic solvent used in an organic synthesis. Among these, THF is more preferable.

In the third step, isoxazole compound (4) from the second step is treated with active metals and hydrogen gas to prepare a compound (5) having an open-ring compound of isoxazole via a hydrogenation. The active metal used in this step procedure includes, but not limited to, Raney Nickel, Pd/C of 10%, and the like. Among these, Raney Nickel is more preferable. Also, a solvent used in the present reaction can be a conventional non-reactive organic solvent used in hydrogenation. Preferably, the mixture of THF and methanol can be used. In addition, it is the most preferable to complete the reaction at room temperature.

In the forth step, isothiazole compound (6) is prepared by adding phosphorus pentasulfide and sodium carbonate to the compound (5), and the reaction is carried out at room temperature, and then 2,3,5.6-tetrachloro-1,4-benzonequinone(chloranil) is added thereto, followed by refluxing. A solvent used in the present reaction can be a conventional non-reactive organic solvent used in an organic synthesis. Among these, tetrahydrafurane is more preferable.

In the last step, the compound of the formula 7 is prepared by adding chlorosulfonic acid to isothiazole compound (6), and cooling to about −5° C., and then the reaction is completed.

Also, the present invention includes a method for preparing the compound of the following formula 1c including the step for reacting the compound of the formula 12 with phosphorus pentasulfide and 2,3,5.6-tetrachloro-1,4-benzoquinone:

Formula 12

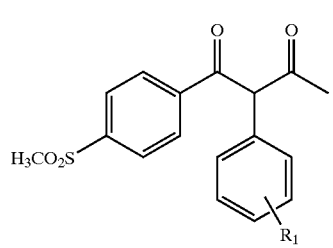

Formula 1c

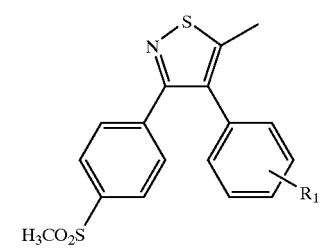

The solvent used in the above reaction includes, but is not limited to, THF, ethyl acetate, DMF and the like.

And the reaction is preferably carried out in the presence of a base and the base can be, but not limited to, sodium carbonate and the like.

Besides, the reaction can be accomplished by reacting at room temperature or by refluxing at boiling point depending upon compounds.

The compound of the formula 12 can be prepared as illustrated schematically in the following reaction formula 2.

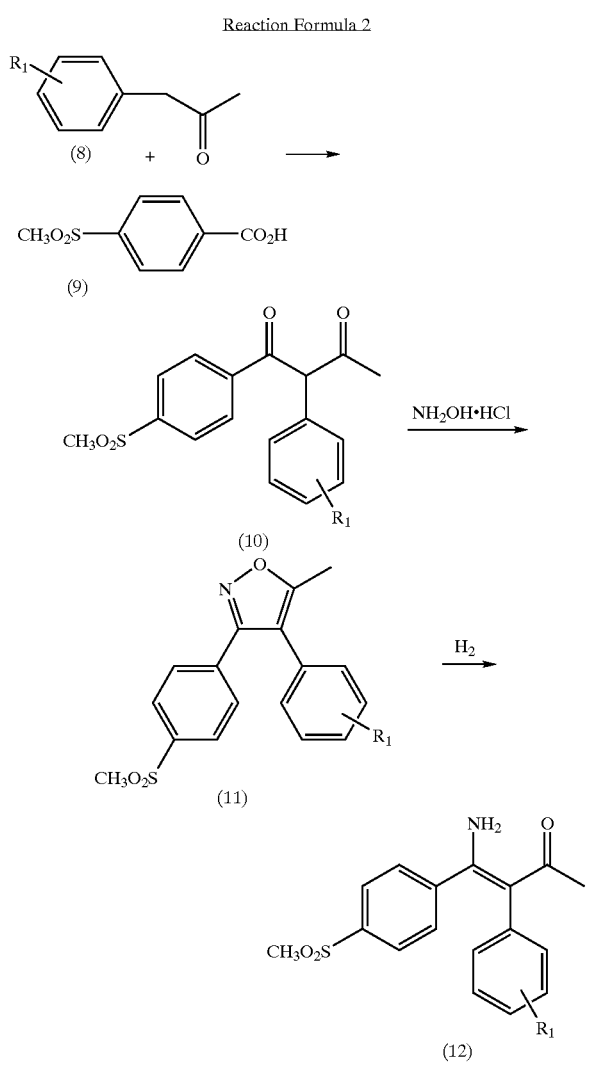

Reaction Formula 2

As demonstrated in the above reaction formula 2, the compound of the formula 12 can be prepared through three steps.

In the first step, 4-methanesulfonyl benzoic acid (9) is reacted with propane-2-one compound (8) substituted with benzyl group on 1 position thereof to prepare the compound of the formula 10. The reaction is carried out in the presence of a base and the base can be selected from, but not limited to, sodium hydroxide, sodium methoxide, sodium t-buthoxide and the like. Among these, sodium hydroxide is most preferable. Also, a solvent used in this step can be a conventional non-reactive organic solvent used in an organic synthesis. Representative examples of such solvents are, but not limited to benzene, toluene, xylene, dimethylformamide, n-methylpyrrolidone and the like. Among these, dimethylformamide is most preferable.

In the second step, the compound of the formula 10 is reacted with hydroxyl amine hydrochloride to prepare the compound of the formula 11. And the reaction can be accomplished under the same condition as the method for preparing the isoxzole compound (4) of the reaction formula 1.

In the last step, the compound of the formula 11 is treated with active metal and hydrogen gas to prepare an opern-ring compound of isoxazole via a hydrogenation. The active metal used in this step includes, but not limited to, Raney Nickel, Pd/C of 10%, and the like. Among these, Raney Nickel is more preferable. Also, this reaction is carried out under the organic solvent used conventionally for hydrogenation. Preferably, the mixture of THF and methanol can be used. In addition, it is the most preferable to complete the reaction at room temperature.

In all the reactions illustrated above, a separation and purification of the resulting products can be processed through a common treatment used in an organic synthesis such as concentration, extraction and the like, and specially, can be carried out by using column chromatography on silica gel phase.

The present invention provides a pharmaceutical composition with antipyretic, analgesic and antiphlogistic activity, including a therapeutically effective amount of an isothiazole derivative or nontoxic salt thereof as an effective component and a pharmaceutically acceptable carrier.

This pharmaceutical composition can be used for antipyretic, analgesic and antiphlogistic agents, which can minimize side effects due to containing the compound of the formula 1 having an activity for selective inhibition against cyclooxygenase-2 or its pharmaceutically acceptable salts.

Conventional non-steroid antiphlogistic agent has showed many side effects, because it inhibits non-selectively cox-1 participating in the secretion of basic endogenous prostaglandin and playing an important role in physiological aspects such as stomach homeostasis, renal blood circulation and so on, as well as cox-2 involving in synthesis of pathological prostaglandin.

On the other hand, the compound of the formula 1 and pharmaceutically acceptable salt thereof has a selective inhibition activity against cox-2, so that they can minimize the side effect that conventional non-steroid antipyretic, analgesic and antiphlogistic agent has showed.

Therefore, the pharmaceutical composition containing the compound of the formula 1 or non-toxic salt thereof, and pharmaceutically acceptable carries or excipients can be a substitute for conventional non-steroid anti-inflammatory drugs. Concretely, it improves side effects of conventional non-steroid antipyretic, analgesic and antiphlogistic agent, and is useful for patients suffering from peptic ulcer, gastritis, partial enteritis, ulcerative colitis, diverticulitis, gastrointestinal haemorrhagia, hypoprothrombinemia and the like.

The pharmaceutical composition according to the present invention is useful for treating all the inflammatory diseases related to pathological prostaglandin, and particularly osteoarthritis and rheumatoid arthritis to be administrated in high amount.

Also, the pharmaceutical composition can be administrated to an adult in an amount of 5 to 400 mg/kg on the basis of a compound of formula 1 or non-toxic salt thereof, but the administration amount can be varied depending upon the seriousness of diseases.

In addition, the pharmaceutical composition can be administrated in a tablet formulation, a forming-tablet formulation, a capsule formulation, a granule formulation, a powder formulation, an extended-release tablet formulation, an extended-release capsule formulation (a single and a multiple unit), an ampul formulation for intravenous and intramusclar injection, an injection formulation, a suspension formulation, a suppository formulation, or any other suitable pharmaceutical formulations.

The extended-release formulation can include an active compound in a full form with initial administration content, or a partial form without initial administration content.

The active compound can be administrated by individual administration method or stepwise administration method by time unit, depending upon existing together therewith, or partially or fully being separated from other ingredients in the formulation.

In case that the active compound is fully separated from other ingredients in the formulation, the active compound is combined to other ingredients, so that in administration unit, it is contained in the same amount or the corresponding weight ratio as being able to exist in the combined mixture.

Especially, the orally administrated pharmaceutical composition including the indicated combined mixture is preferable.

In order to prepare the pharmaceutical formulation including the combined mixture, the active compound is formulated in the indicated amount by a preferable method with excipients, diluents and/or adjuvants having physiological tolerance.

The examples of the excipients, and adjuvants are natural sugar such as gelatin, saccharose and lactose, lecithin, pectin, starch such as cornstarch, amylose, cyclodextrin, cyclodextrin's derivative, dextran, polyvinylpyrrolidone, polyvinylacetate and gum Arabic, alginic acid, talc, salicylic acid, calcium hydrogen phosphate, cellulose, cellulose's derivative such as methoxypropylcellulose, methylcellulose, hydroxypropylmethylcellulose, hydroxypropylmethylcellulose phthalate, $C_{12}$–$C_{22}$ fatty acids, emulsifying agent, oil and fatty, especially, vegetable glycerol ester of saturated fatty acid and polyglycerol ester, monohydric or polyhydric alcohols and polyglycol such as polyethylene glycol, $C_1$–$C_{20}$ aliphatic alcohol, or ester of aliphatic saturated or unsaturated $C_2$–$C_{22}$ fatty and polyhydric alcohols such as glycol, glycerol, diethylene glycol, 1,2-propylene glycol, sorbitol.

Additionally, the suitable adjuvants are disintergrant, cross-linked polyvinylpyrrolidone, sodium carboxymethyl starch, sodium carboxymethyl cellulose and microcrystalline cellulose. And the disclosed coating material such as acrylic acid, methacrylic acid, and/or ester polymer and copolymer thereof, zein, ethylcellulose, ethylcellulose succinate, shellac and the like can be used.

Suitable plasticizer as the coating material can be ester of citric acid and tartaric acid, glycerol and ester of glycerol, and polyethylene glycol having diverse chain length. In preparing the solution or suspension, water or physiologically acceptable organic solvents such alcohol and aliphatic alcohol can be used suitably.

In the liquid formulation, preservatives such as potassium sorbate, methyl 4-hydroxybenzoate and propyl 4-hydroxybenzoate, antioxidant such as ascorbic acid, and aromatic such like peppermint oil can be used.

In preparing the formulation, the disclosed conventional dissolvent such as polyvinylpyrrolidone and polysorbate 80, and emulsifying agent can be used.

Any other examples of the suitable excipients and adjuvants are referred in "Lexikon der Hilfsstoffe fur Pharmazie, Kosmetik und angrenzende Gebiete (Encyclopaedia of auxiliaries for pharmacy, cosmetics and related fields)" by Dr. H. P. Fiedler.

DETAILED DESCRIPTION OF THE PREFERRED OF EMBODIMENT

Practical and presently preferred embodiments of the present invention are illustrated as shown in the following Examples.

However, it will be appreciated that those skilled in the art, on consideration of this disclosure, may make modifications and improvements within the spirit and scope of the present invention.

REFERENCE EXAMPLE 1

Preparation of 1,2-diphenyl-ethanone oxime

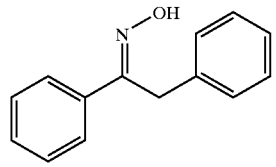

Formula 13

20 g of dioxybenzoin was dissolved in anhydrous ethanol 100 ml, and 9.21 g of hydroxylamine hydrochloride and 7.43 g of potassium hydroxide was added thereto, and then the solution was refluxed for 6 hours to complete the reaction. The reaction solution was cooled to room temperature, diluted in water 200 ml and extracted with ethyl acetate to separate an organic layer. The separated organic layer was dried with anhydrous magnesium sulfate and the solvent was evaporated under reduced pressure to yield a light yellow liquid phase. The liquid phase was re-crystallized in ethanol and water. As a result, 17.7 g of the compound of the formula 13 (yield: 82%) was obtained as a solid phase.

$^1$H-NMR(400 MHz, CDCl$_3$) 4.12(s, 2 H), 7.10–7.15(m, 1 H), 7.20–7.30(m, 4 H), 7.40–7.50(m, 3 H), 7.60–7.65(m, 2 H), 8.20(bs, 1 H)

Melting Point: 87–90° C.

REFERENCE EXAMPLE 2

Preparation of 1-(4-bromophenyl)-2-phenyl-ethanone oxime

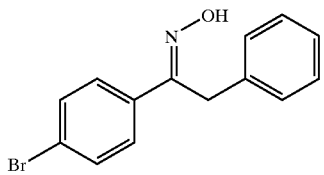

Formula 14

The reaction was carried out through the same method as Reference Example 1, except employing 2.0 g of 1-(4-bromo phenyl)-2-phenyl ethanone instead of dioxybenzoin. As a result, 1.53 g of the compound of the formula 14 (yield: 75%) was obtained as a light color solid phase.

$^1$H NMR (400 MHz, CDCl$_3$) 4.12(s, 2 H), 7.05–7.10(m, 1 H), 7.19(d, 2 H, J=8.2 Hz), 7.30–7.38(m, 4 H), 7.50(d, 2 H, J=8.2 Hz), 8.20(bs, 1 H)

Melting Point: 122–125° C.

REFERENCE EXAMPLE 3

Preparation of 1-(4-methoxyphenyl)-2-phenyl-ethanone oxime

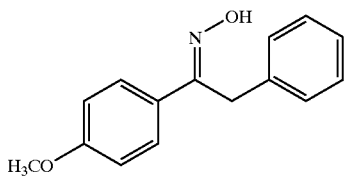

Formula 15

The reaction was carried out through the same method as Reference Example 1, except employing 10 g of 1-(4-methoxy phenyl)-2-phenyl ethanone instead of dioxybenzoin. As a result, 0.58 g of the compound of the formula 15(yield: 54%) was obtained as a light color solid phase.

$^1$H NMR (400 MHz, CDCl$_3$) 3.90 (s, 3 H), 4.12(s, 2 H), 6.90 (d, 2 H, J=8.4 Hz), 7.05–7.10(m, 1 H), 7.30–7.38(m, 4 H), 7.50(d, 2 H, J=8.4 Hz), 8.18(bs, 1 H)

Melting Point: 132–135° C.

REFERENCE EXAMPLE 4

Preparation of 1-(4-fluorophenyl)-2-phenyl-ethanone oxime

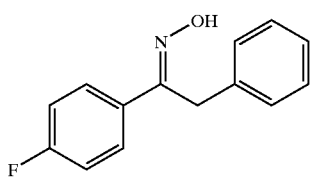

Formula 16

The reaction was carried out through the same method as Reference Example 1, except employing 2.0 g of 1-(4-flourophenyl)-2-phenyl ethanone instead of dioxybenzoin. As a result, 1.35 g of the compound of the formula 16 (yield: 63%) was obtained as a light color solid phase.

$^1$H NMR (400 MHz, CDCl$_3$) 4.12(s, 2 H), 7.05–7.15(m, 3 H), 7.30–7.38(m, 4 H), 7.40(d, 2 H, J=8.4 Hz), 8.15(bs, 1 H)

Melting Point: 100–103° C.

REFERENCE EXAMPLE 5

Preparation of 5-methyl-3,4-diphenyl-isoxazole

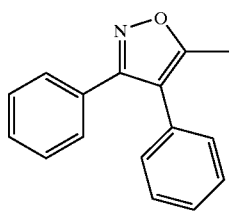

Formula 17

4 g of 1,2-diphenyl-ethanone oxime from Reference Example 1 was introduced into the container, and anhydrous THF 20 ml was added to the container under a nitrogen blanket, and the 1,2-diphenyl-ethanone oxime solution was cooled to −78° C. And 2.05 equivalent of n-butyl lithium was slowly added to the solution. Then, the solution was refluxed at the same temperature for 1 hour, warmed up to room temperature, and refluxed one more hour at the room temperature. After the reflux, 1.1 equivalent of anhydrous acetic acid was added thereto, and then stirred at room temperature for 2 hours. After completing the reaction, 50 ml of water was added thereto, and extracted with ethyl acetate to separate an organic layer. The separated organic layer was dried with anhydrous magnesium sulfate, and a solvent was evaporated under reduced pressure to obtain a liquid in oil phase. The liquid was directly dissolved in 50 ml of dichloromethane, and then 3 ml of a concentrated sulfuric acid was added thereto, and then refluxed for 3 hours. After completing the reaction, 100 ml of water was added thereto, and extracted with dichloromethane to separate an organic layer. The separated organic layer was dried with anhydrous magnesium sulfate, and a solvent was evaporated under reduced pressure to obtain a liquid in oil phase. The liquid was purified through a column chromatography with a mixture of ethylacetate and normal hexane in the ratio of 1:30. As a result, 2.50 g of the compound of the formula 17 (yield: 56%) was obtained as a liquid phase.

Mass (LOW EI)=235.11

REFERENCE EXAMPLE 6

Preparation of 3-(4-bromophenyl)-5-methyl-4-isoxazole

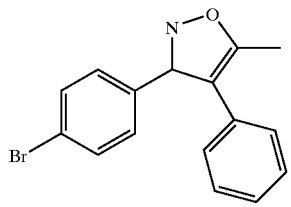

Formula 18

The reaction was carried out through the same method as Reference Example 5, except employing the compound of Reference Example 2, 2 g of 1-(4-bromophenyl)-2-phenyl ethanone oxime instead of 1,2-diphenyl-ethanone oxime. As a result, 1.05 g of the compound of the formula 18 (yield: 51%) was obtained as a liquid phase.

$^1$H-NMR (400 MHz, CDCl$_3$) 2.51(s, 3 H), 7.32-7.38(m, 5 H), 7.45–7.50(m, 4 H)

REFERENCE EXAMPLE 7

Preparation of 3-(4-methoxyphenyl)-5-methyl-4-phenyl-isoxazole

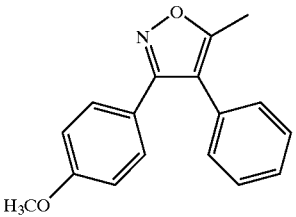

Formula 19

The reaction was carried out through the same method as Reference Example 5, except employing 0.5 g of 1-(4- methoxyphenyl)-2-phenyl ethanone oxime of Reference Example 3, instead of 1,2-diphenyl-ethanone oxime. As a result, 0.26 g of the compound of the formula 19 (yield: 48%) was obtained as a liquid phase.

Mass (LOW EI)=265.1

REFERENCE EXAMPLE 8

Preparation of 3-(4-fluorophenyl)-5-methyl-4-phenyl-isoxazole

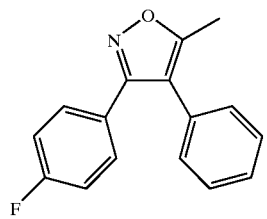

Formula 20

The reaction was carried out through the same method as Reference Example 5, except employing 1.5 g of 1-(4-fluorophenyl)-2-phenyl ethanone oxime of the compound of Reference Example 4, instead of 1,2-diphenyl-ethanone oxime. As a result, 0.99 g of the compound of the formula 20 (yield: 60%) was obtained as a liquid phase.

Mass (LOW EI)=253.1

REFERENCE EXAMPLE 9

Preparation of 2-(4-fluorophenyl)-1-(4-methanesulfonylphenyl)-butane-1,3-dione

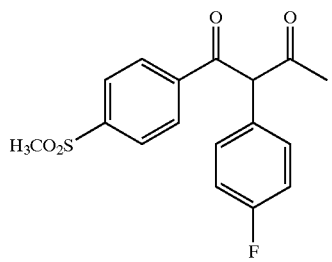

Formula 21

2 g of 1-(4-fluorophenyl)-propane-2-one, 2.0 g of 4-methanesulfonyl benzoic acid and 1.67 g of carbonyl diimidazole was mixed and dissolved in 10 ml of dimethylformamide. And then, 0.8 g of sodium hydride was slowly added to the solution, and then refluxed for 2 hours. After completing the reaction, 100 ml of water was added thereto, and then extracted with dichloromethane to separate an organic layer. The separated organic layer was dried with anhydrous magnesium sulfate, and a solvent was evaporated under reduced pressure. As a result, 2.46 g of the compound of the formula 21 (yield: 56%) was obtained as a liquid phase.

REFERENCE EXAMPLE 10

Preparation of 4-(4-fluorophenyl)-3-(4-methanesulfonylphenyl)-5-methyl-isoxazol

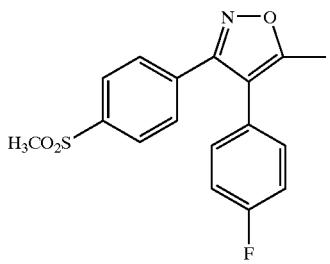

Formula 22

500 mg of 2-(4-fluorophenyl)-1-(4-methanesulfonylphenyl)-butane-1,3-dione from Reference Example 5 was dissolved in 10 ml of ethanol, and then 115 mg of hydroxylamine hydrochloride and 136 mg of sodium acetate were added thereto, and then refluxed for 8 hours. After completing the reaction, 20 ml of water was added thereto, and then extracted with ethyl acetate to separate an organic layer. The organic layer was dried with anhydrous magnesium sulfate, and a solvent was evaporated under reduced pressure to yield a liquid in oil phase. The liquid was purified through a column chromatography with ethylacetate and normal hexane in the ratio of 1:10. As a result, 370 mg of the compound of the formula 22 (yield: 75%) was obtained as a white solid phase.

$^1$H NMR (400 MHz, CDCl$_3$) 2.34(s, 3 H), 3.00(s, 3 H), 7.19(dd, 2H, J=8.2, 2.2 Hz), 7.7.25(dd, 2 H, 8.2, 2.2 Hz), 7.7 (d, 2 H, J=8.3 Hz), 7.8 (d, 2 H, J=8.3 Hz)

Melting Point=120–123° C.

REFERENCE EXAMPLE 11

Preparation of 5-methyl-3,4-diphenyl-isothiazole

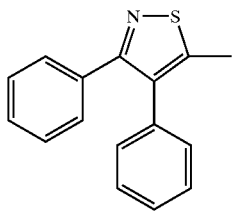

Formula 23

500 mg of 5-methyl-3,4-diphenyl-isoxazole was dissolved in 30 mg of methanol, and then 250 mg of Raney nickel and 300 mg of sodium hydroxide were added to the solution in sequence, and then refluxed under 1 atm of a hydrogen blanket for 6 hours at room temperature. After completing the reaction of the first stage, the remained solid reactant was filtrated and removed, and the solution was distilled under reduced pressure to yield a liquid in oil phase. The liquid was introduced to the reactor, and 10 ml of anhydrous THF, 225 mg of phosphorus pentasulfide and 125 mg of NaHCO$_3$ were sequentially added to the reactor under a nitrogen blanket, and then stirred at room temperature for 12 hours. After that, 330 mg of tetrachloro-1,4-diquinolon was added thereto, and refluxed for 12 hours. After completing the reaction of the second stage, 20 ml of water was added thereto, and then extracted with ethyl acetate to separate an organic layer. And the organic layer was dried with anhydrous magnesium sulfate and a solvent was evaporated under reduced pressure to obtain a liquid in oil phase. The liquid was purified through a column chromatography with ethylacetate and normal hexane in the ratio of 1:10. As a result, 304 mg of the compound of the formula 11 (yield: 57%) was obtained as a yellow liquid phase.

$^1$H NMR(400 MHz, CDCl$_3$)

2.43(s, 3 H), 7.12–7.15(m, 2 H), 7.20–7.25(m, 4 H), 7.30–7.35(m, 4 H)

REFERENCE EXAMPLE 12

Preparation of 3-(4-bromophenyl)-5-methyl-4-phenyl-isothiazole

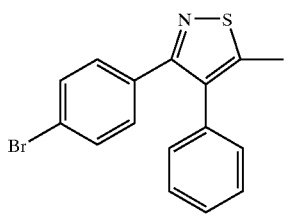

Formula 24

The reaction was carried out through the same method as the Reference Example 11, except 500 mg of employing 3-(4-bromophenyl)-5-methyl-4-phenyl-isoxazole instead of 5-methyl-3,4-diphenyl-isoxazole. As a result, 289 mg of the compound of the formula 24 (yield: 55%) was obtained as a yellow liquid phase.

$^1$H NMR(400 MHz, CDCl$_3$) 2.43 (s, 3 H) , 7.12–7.15 (m, 2 H), 7.20–7.25 (m, 4 H), 7.40–7.48 (m, 3 H)

REFERENCE EXAMPLE 13

Preparation of 3-(4-methoxyphenyl)-5-methyl-4-phenyl-isothiazole

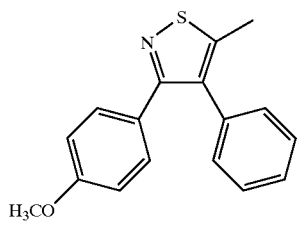

Formula 25

The reaction was carried out through the same method as the Reference Example 11, except employing 400 mg of 3-(4-methoxyphenyl)-5-methyl-4-phenyl-isoxazole instead of 5-methyl-3,4-diphenyl-isoxazole. As a result, 233 mg of the compound of the formula 25 (yield: 55%) was obtained as a yellow liquid phase.

$^1$H NMR(400 MHz, CDCl$_3$) 2.43 (s, 3 H), 3.90 (s, 3 H), 6.96 (d, 2 H, J=8.4 Hz), 7.05–7.10(m, 1 H), 7.30–7.38(m, 4 H), 7.45 (d, 2 H, J=8.4 Hz)

REFERENCE EXAMPLE 14

Preparation of 3-(4-fluorophenyl)-5-methyl-4-phenyl)-isothiazole

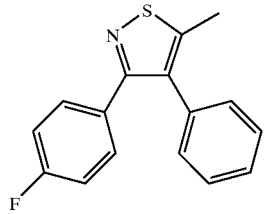

Formula 26

The reaction was carried out through the same method as the Reference Example 11, except employing 900 mg of 3-(4-fluorophenyl)-5-methyl-4-phenyl-isoxazole instead of 5-methyl-3,4-diphenyl-isoxazole. As a result, 570 mg of the compound of the formula 25 (yield: 60%) was obtained as a yellow liquid phase.

$^1$H NMR(400 MHz, CDCl$_3$) 2.43 (s, 3 H), 3.95 (s, 3 H), 7.05–7.15(m, 3 H), 7.30–7.38(m, 4 H), 7.40(d, 2 H, J=8.4 Hz)

EXAMPLE 1

Preparation of 4-(4-fluorophenyl)-3-(4-methanesulfonyl)-5-methyl-isothiazole

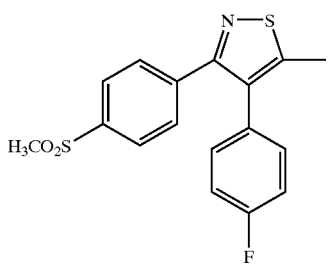

Formula 27

500 mg of 4-(4-fluorophenyl)-3-(4-methanesulfonylphenyl)-5-methyl-isoxazole from Reference Example 10 was dissolved in 30 ml of methanol, and 250 mg of Raney nickle and 300 mg of sodium hydroxide were added thereto in sequence, and then stirred under 1 atm of hydrogen blanket for 6 hours at room temperature. After completing the reaction of the first stage, the remained solid reactants were filtrated and removed, and then the solution was distilled under reduced pressure to yield a liquid in oil phase. The liquid was introduced into the reactor, and 10 ml of anhydrous tetrahydrofuran(THF), 225 mg of phosphorus pentasulfide and 125 mg of NaHCO$_3$ were sequentially added to the reactor under a nitrogen blanket, and then stirred at room temperature for 12 hours. After that, 330 mg of 2,3,5,6-tetrachloro-1,4-benzoquinon was added thereto, and refluxed for 12 hours. After completing the reaction of the second stage, 20 ml of water was added thereto, and then extracted with ethyl acetate to separate an organic layer. The organic layer was dried with anhydrous magnesium sulfate and a solvent was evaporated under reduced pressure to yield a liquid in oil phase. The liquid was purified through a column chromatography with ethyl acetate and normal hexane in the ratio of 1:10. As a result, 235 mg of the compound of the formula 27 (yield: 45%).

$^1$H NMR (400 MHz, CDCl$_3$) 2.34(s, 3 H), 3.20(s, 3 H), 7.19(dd, 2H, J=8.2, 2.2 Hz), 7.25(dd, 2 H, 8.2, 2.2 Hz), 7.70(d, 2 H, J=8.3 Hz), 7.82(d, 2 H, J=8.3 Hz)

EXAMPLE 2

Preparation of 4-(5-methyl-3-phenyl-isothiazole-4-yl)-benzenesulfonamide

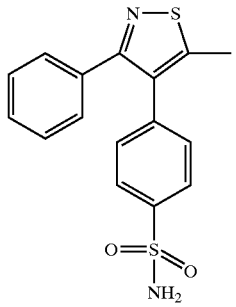

Formula 28

800 mg of 5-methyl-3,4-diphenyl-isothiazole from Reference Example 11 was introduced to the reactor, and cooled to 0° C., and 5 ml of chlorosulfonic acid was slowly added thereto. The reactants were stirred at the same temperature for 2 hours. After completing the reaction of the first stage, 100 ml of ice water was slowly added thereto, and extracted with 50 ml of dichloromethane. And then, 50 ml of ammonium water was added thereto and stirred drastically for 1 hour at room temperature. After completing the reaction of the second stage, 100 ml of ice water was slowly added thereto, and extracted with 50 ml of dichloromethane to separate an organic layer. The organic layer was dried with anhydrous magnesium sulfate and a solvent was evaporated under reduced pressure. A prepared liquid in oil phase was re-crystallized through a column chromatography with the mixture solution of ethyl acetate and normal hexane. As a result, 631 mg of the compound of the formula 28 (yield: 60%) was obtained as a yellow solid phase.

$^1$H NMR (300 MHz, CDCl$_3$) 2.50(s, 3 H), 7.20–7.45(m, 9 H), 7.78(d, 2 H, J=8.3 Hz)

Melting Point: 173–175° C.

EXAMPLE 3

Preparation of 4-[3-(4-bromophenyl)-5-methyl-isothiazole-4-yl]-benzenesulfonamide

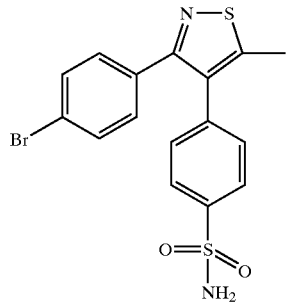

Formula 29

The reaction was carried out through the same method as Example 2, except employing 800 mg of 3-(4-bromophenyl)-5-methyl-4-phenyl isothiazole the compound of Reference Example 12, instead of 5-methyl-3,4-diphenyl-isothiazole. As a result, 634 mg of the compound of formula 30 (yield: 64%) was obtained as a yellow solid phase.

$^1$H NMR(400 MHz, DMSO-d$_6$) 2.48(s, 3 H), 7.30(d, 2 H, J=8.5 Hz), 7.42(s, 2 H), 7.53 (d, 2 H, J=8.5 Hz) , 7.62 (d, 2 H, J=8.5 Hz), 7.80(d, 2 H, J=8.5 Hz)

Melting Point: 217–220° C.

EXAMPLE 4

Preparation of 4-[3-(4-methoxyphenyl)-5-methyl-isothiazole-4-yl]-benzenesulfonamide

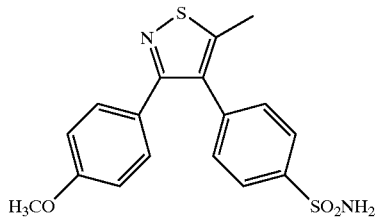

Formula 30

The reaction was carried out through the same method as the Example 2, except employing 300 mg of 3-(4-methoxyphenyl)-5-methyl-4-phenyl isothiazole of the compound of Reference Example 13, instead of 5-methyl-3,4-diphenyl-isothiazole. As a result, 310 mg of the compound of the formula 30 (yield: 74%) was obtained as a yellow solid phase.

$^1$H NMR(400 MHz, DMSO-d$_6$) 2.48(s, 3 H), 3.90 (s, 3 H), 6.94 (d, 2 H, J=8.4 Hz), 7.42(s, 2 H), 7.46 (d, 2 H, J=8.4 Hz), 7.53(d, 2 H, J=8.5 Hz),7.95 (d, 2 H, J=8.5 Hz)

EXAMPLE 5

Preparation of 4-[3-(4-fluorophenyl)-5-methyl-isothiazole-4-yl]-benzenesulfonamide

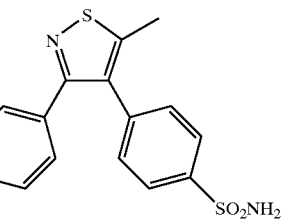

Formula 31

The reaction was carried out through the same method as Example 2, except exploiting 900 mg of 3-(4-fluorophenyl)-5-methyl-4-phenyl isothiazole of the compound of Reference Example 14, instead of 5-methyl-3,4-diphenyl-isothiazole. As a result, 725 mg of the compound of formula 31 (yield: 66%) was obtained as a yellow solid phase.

$^1$H NMR(400 MHz, DMSO-d$_6$) 2.48 (s, 3 H), 3.80 (s, 3 H), 7.30 (d, 2 H, J=7.0 Hz), 7.45–7.60 (m, 6 H), 8.00 (d, 2 H, J=7.0 Hz)

EXAMPLE 6

Preparation of 4-(4-methanesulfonylphenyl)-5-methyl-3-phenyl-isothiazole

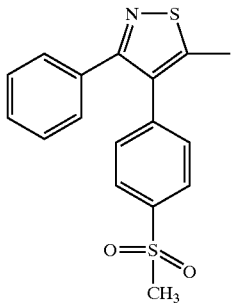

Formula 32

700 mg of 5-methyl-3,4-diphenyl-isothiazole from Reference Example 11 was introduced to the reactor, and cooled to 0° C., and 5 ml of chlorosulfonic acid was slowly added to the reactor. The reactants were stirred at the same temperature for 2 hours. After completing the reaction of the first stage, 100 ml of ice water was slowly added to the reacting product, and extracted with 50 ml of dichloromethane to separate an organic layer. The organic layer was dried with the anhydrous magnesium sulfate and a solvent was evaporated under reduced pressure. The obtained product was dissolved in 10 ml of anhydrous tetrahydrafuran (THF), and 3 ml of hydrazine was added to the solution at 0° C. m, and stirred for 10 minutes. After evaporating THF, the product was dissolved in 10 ml of ethanol, and 1.2 g of sodium acetate and 2.1 g of methyl iodide were added thereto, and then refluxed for 12 hours. After completing the reaction of the second stage, 100 ml of water was added thereto, and extracted with ethyl acetate to separate an organic layer. The organic layer was dried with anhydrous magnesium sulfate and a solvent was evaporated to separate an organic layer. A liquid in oil phase was re-crystallized with the mixture of ethyl acetate and normal hexane. As a result, 462 mg of the compound of the formula 32 (yield: 50%) was obtained as a yellow solid.

$^1$H NMR (300 MHz, CDCl$_3$) 2.50(s, 3 H), 3.10(s, 3 H), 7.15–7.23(m, 5 H), 7.27(d, 2 H, J=8.7 Hz), 7.80(d, 2 H, J=8.7 Hz)

Melting Point: 162–165° C.

EXAMPLE 7

Preparation of 3-(4-bromophenyl)-4-(4-methanesulfonylphenyl)-5-methyl-isothiazole

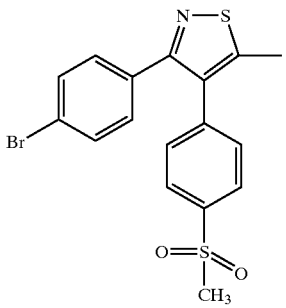

Formula 33

The reaction was carried out through the same method as Example 6, except employing 600 mg of 3-(4-bromophenyl)-5-methyl-4-phenylisothiazole of the compound of Reference Example 12, instead of 5-methyl-3,4-diphenyl-isothiazole. As a result, 407 mg of the compound of the formula 33 (yield: 55%) was obtained as a yellow solid phase.

$^1$H NMR(400 MHz, CDCl$_3$) 2.50(s, 3 H), 3.12(s, 3 H), 7.30(d, 2 H, J=8.5 Hz), 7.53(d, 2 H, J=8.5 Hz), 7.52(d, 2 H, J=8.4 Hz), 7.75(d, 2 H, J=8.4 Hz)

mp=200–205° C.

EXAMPLE 8

Preparation of 3-(4-methoxyphenyl)-4-(4-methanesulfonylphenyl)-5-methyl-isothiazole

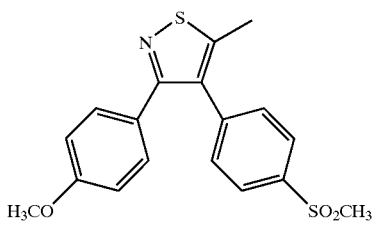

Formula 34

The reaction was carried out through the same method as Example 6, except employing 600mg of 3-(4-methoxyphenyl)-5-methyl-4-phenylisothiazole of the compound of Reference Example 13, instead of 5-methyl-3,4-diphenyl-isothiazole. As a result, 387 mg of the compound of the formula 34 (yield: 50%) was obtained as a yellow solid phase.

$^1$H NMR(400 MHz, CDCl$_3$) 2.50 (s, 3 H), 3.12 (s, 3 H), 3.98 (s, 3 H) 7.00 (d, 2 H, J=8.9 Hz), 7.30 (d, 2 H, J=8.9 Hz), 7.60 (d, 2 H, J=8.6 Hz), 7.95 (d, 2 H, J=8.6 Hz)

EXAMPLE 9

Preparation of 3-(4-fluorophenyl)-4-(4-methanesulfonyl)-5-methyl-isothiazole

Formula 35

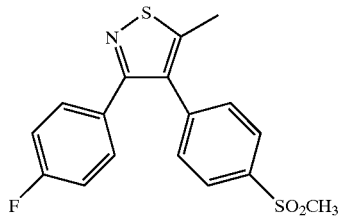

The reaction was carried out through the same method as Example 6, except employing 500 mg of 3-(4-fluorophenyl)-5-methyl-4-phenylisothiazole of the compound of Reference Example 14, instead of 5-methyl-3,4-diphenyl-isothiazole. As a result, 287 mg of the compound of the formula 35 (yield: 45%) was obtained as a yellow solid phase.

$^1$H NMR(400 MHz, CDCl$_3$) 2.50 (s, 3 H), 3.12 (s, 3 H), 7.20 (d, 2 H, J=7.0 Hz), 7.45 (dd, 2 H, J=7.0, 10.2 Hz), 7.60 (d, 2 H, J=8.7 Hz), 8.00 (d, 2 H, J=8.7 Hz)

PHARMACOLOGICALLY EXPERIMENTAL EXAMPLE

The Selective Inhibition Activity against Cyclooxygenase-2

(1) Experimental Procedure

In order to investigate pharmacologically the selective inhibition activity against cyclooxygenase-2 enzyme, the inhibitive effects against cyclooxygenase-1 and cyclooxygenase-2 were measured by two methods as follows.

i) Analysis of the Inhibitive Effects against the Cyclooxygenase-1 using U-937

A cultured U-937 (humane lymphoma cell with Deposit No. 21593, obtained from Korean cell line bank) was centrifuged to collect the pellet. Then, the pellet was diluted with 1×HBSS(Hank's balanced salt solution) at the concentration of 1×10$^6$ cells/ml, and 1 ml of them was transferred into each of 12-well plates.

And then, 5 μl of 1 μM detecting solution prepared by diluting in DMSO and 5 μl of DMSO vehicle were added thereto and mixed, and the mixture was cultured at 37° C. in CO$_2$ incubator for 15 minutes. Arachidonic acid as a substrate was dissolved in ethanol to prepare a stock solution with a concentration of 10 mM, followed by diluting with 1×HBSS to prepare the solution of 1 mM. 10 μl of 1 mM Arachidonic acid solution was added to each of the treated wells and the mixture was cultured at 37° C. in CO$_2$ incubator for 30 minutes. The cell solution of each well was collected in the centrifuge tube and centrifuged at 4° C., for 5 minutes at 10,000 rpm. As PGE2 existed in the supernatant separated from collected cell, the concentration of PGE2 was quantitated by using monoclonal kit from Cayman Chemicals, and the concentration of samples and DMSO vehicle were compared to estimate the inhibition ratio (%) of each compound against cyclooxygenase-1. Ultimately, the inhibition effect against the cyclooxygenase-1 enzyme was obtained from the result.

ii) Analysis of the Inhibitive Effects against the Cyclooxygenase-2 using Raw 264.7.

After seeding 2×10$^6$ cells of Raw 264.7 cell (obtained from Korean cell line bank, Deposit No. 40071) into each of 12-well plates, the wells were treated with 250 μM aspirin and cultured at 37° C. in CO$_2$ incubator for 2 hours, and then was replaced with new media, treated with each 10 nM detecting sample, and cultured for 30 minutes. In addition, the samples were treated with 100 units/ml of interferon ɣ and 100 ng/ml of lipopolysaccharide(LPS), and cultured for 18 hours. Then, the media was transferred to other test tubes and PGE 2 was quantitated by using EIA kit (Cayman Chemicals).

(2) Experimental Results

The % inhibition was calculated as follows, and the results were described in Table 1.

% inhibition={(PGE2 concentration compensated with interferon ɣ and LPS-PGE2 concentration compensated with analysis sample)/(PGE2 concentration compensated with interferon ɣ and LPS)}×100

TABLE 1

Inhibitory effects of cyclooxygenase (COX) (unit: % inhibition)

| Examples | COX-1 (10 μM) | COX-2 (30 nM) |
|---|---|---|
| Standard Substance (Celecoxib) | 84.0 | 65.7 |
| 1 | 29.8 | 63.7 |
| 2 | 35.5 | 60.2 |
| 3 | 38.8 | 58.5 |
| 4 | 79.5 | 67.7 |
| 5 | 77.8 | 72.3 |
| 6 | 56.4 | 69.0 |
| 7 | 45.7 | 65.6 |
| 8 | 80.1 | 76.4 |
| 9 | 67.2 | 65.1 |

(3) Evaluation

In vitro experimental results for the inhibition of cyclooxygenase-1 and cyclooxygenase-2 were observed as follows.

Consequently, in case of the compounds of Example 1~9, the ratio of the inhibition % of cyclooxygenase-2 to cyclooxygenase-1 was much higher than the standard substance (Celecoxib). That is to say, it is shown that the selective inhibition of cyclooxygenase-2 against cyclooxygenase-1 is better than that of any other standard substances.

As demonstrated and confirmed above, the novel compound of the present invention is a drug substitute improving side effects of anti-inflammatory drug in conventional non-steroids, and is useful for patients suffering from peptic ulcer, gastritis, partial enteritis, ulcerative colitis, diverticulitis, gastrointestinal haemorrhagia, hypoprothrombinemia and the like. Besides, it is expected to be useful for treating inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

What is claimed is:

1. An isothiazole derivative of the formula 1 or nontoxic salt thereof:

Formula 1

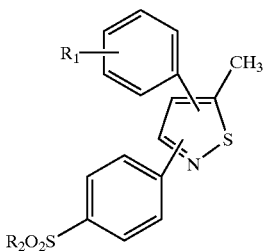

wherein, $R_1$ is hydrogen, alkoxy or halogen; and $R_2$ is methyl or amino group.

2. The isothiazole derivative or nontoxic salt thereof according to claim 1, wherein said isothiazole derivative is selected from a group consisting of:
4-(4-fluorophenyl)-3-(4-methanesulfonylphenyl)-5-methyl-isothiazol,
4-(5-methyl-3-phenyl-isothiazole-4-yl)-benzonesulfonamide,
4-[3-(4-bromophenyl)-5-methyl-isothiazIole-4-yl]-benzenesulfonamide,
4-[3-(4-methoxyphenyl)-5-methyl-isothiazole-4-yl]-benzenesulfonamide,
4-[3-(4-fluorophenyl)-5-methyl-isothiazole-4-yl]-benzenesulfonamide,
4-(4-methanesulfonylphenyl)-5-methyl-3-phenyl-isothiazole,
3-(4-bromophenyl)4-(4-methanesulfonylphenyl)-5-methyl-isotiazole,
3-(4-methoxyphenyl)-4-(4-methanesulfonylphenyl)-5-methyl-isothiazole, and
3-(4-fluorophenyl)-4-(4-methanesulfonylphenyl)-5-methyl-isothiazole.

3. A pharmaceutical composition with antipyretic, analgesic and antiphiogistic activity, including a therapeutically effective amount of an isothiazole derivative or nontoxic salt thereof according to claim 1 or 2 as an effective component and a pharmaceutically acceptable carrier.

* * * * *